(12) United States Patent
Montagnino et al.

(10) Patent No.: US 6,538,215 B2
(45) Date of Patent: *Mar. 25, 2003

(54) PROGRAMMABLE DIGITAL SCALE

(75) Inventors: James G. Montagnino, St. Charles, IL (US); Evan T. Ward, Chicago, IL (US); Noah E. A. Dingler, Richfield, MN (US)

(73) Assignee: Sunbeam Products, Inc., Boca Raton, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/482,785

(22) Filed: Jan. 13, 2000

(65) Prior Publication Data

US 2002/0134589 A1 Sep. 26, 2002

(51) Int. Cl.[7] .......................... G01G 19/40; A61B 5/05; G06F 17/00
(52) U.S. Cl. .................. 177/25.16; 177/25.19; 600/547; 702/173; 128/921
(58) Field of Search .......................... 177/25.16, 25.19; 600/547; 702/173; 128/921

(56) References Cited

U.S. PATENT DOCUMENTS

| | | | | |
|---|---|---|---|---|
| 3,967,690 A | * | 7/1976 | Norhcutt ................ | 177/25.16 |
| 4,113,039 A | * | 9/1978 | Ozaki et al. ............. | 177/25.16 |
| 4,301,879 A | * | 11/1981 | Dubow .................... | 177/25.19 |
| 4,318,447 A | * | 3/1982 | Northcutt ................ | 177/25.16 |
| 4,364,442 A | | 12/1982 | Flickinger .............. | 177/177 |
| 4,366,873 A | * | 1/1983 | Levy et al. .............. | 177/25.16 |
| 4,423,792 A | * | 1/1984 | Cowan ..................... | 177/25.16 |
| 4,576,244 A | * | 3/1986 | Zeigner et al. .......... | 177/25.16 |
| 4,577,710 A | * | 3/1986 | Ruzumna ................. | 177/25.16 |
| 4,850,365 A | | 7/1989 | Rosenthal ................ | 128/664 |
| 4,858,709 A | | 8/1989 | Stahl ...................... | 177/164 |
| 4,895,163 A | | 1/1990 | Libke et al. ............. | 177/734 |
| 4,951,197 A | * | 8/1990 | Melinger ................. | 600/300 |
| 5,415,176 A | * | 5/1995 | Sato et al. .............. | 177/245 |
| 5,449,000 A | | 9/1995 | Libke et al. ............. | 177/734 |
| 5,579,782 A | * | 12/1996 | Masuo .................... | 600/547 |
| 5,646,376 A | * | 7/1997 | Kroll et al. ............. | 177/211 |
| 5,673,691 A | * | 10/1997 | Abrams et al. .......... | 600/300 |
| 5,796,640 A | * | 8/1998 | Sugarman et al. ....... | 708/132 |
| 5,819,735 A | * | 10/1998 | Mansfield et al. ...... | 600/300 |
| 5,839,901 A | * | 11/1998 | Karkanen ................ | 434/127 |
| 5,886,302 A | | 3/1999 | Germanton et al. ..... | 177/139 |
| 5,890,128 A | * | 3/1999 | Diaz et al. .............. | 705/2 |
| 6,038,465 A | * | 3/2000 | Melton, Jr. ............. | 177/25.19 |
| 6,083,006 A | * | 7/2000 | Coffman ................. | 434/127 |
| 6,088,615 A | * | 7/2000 | Masuo .................... | 600/547 |
| 6,208,890 B1 | * | 3/2001 | Sarrazin et al. ......... | 600/547 |
| 6,256,532 B1 | * | 7/2001 | Cha ........................ | 600/547 |

* cited by examiner

Primary Examiner—Randy W. Gibson
(74) Attorney, Agent, or Firm—Kramer, Levin, Naftalis & Frankel LLP

(57) ABSTRACT

A programmable microprocessor-controlled digital scale capable of storing profiles of multiple users and respective user-specific weight management information includes a software program executed by the microprocessor to create and store a user profile for each user. The software program also allows the generation user-specific weight control information based on the user's profile and weight, and displays the information to the user. The generated user-specific weight control information can include, for example: current weight; absolute as well as percentage change in weight; graph of the minimum and maximum weight for the average person matching the user's profile; a thirty day rolling graph of the user's weight history; information about the number of calories that should be consumed in order to either maintain weight, or lose one pound per week; and body fat measurements.

23 Claims, 4 Drawing Sheets

PROGRAMMABLE DIGITAL SCALE

FIELD OF THE INVENTION

The present invention relates to an electronic digital bathroom scale, specifically to a programmable digital scale that measures weight and also provides the user with personalized weight management information.

BACKGROUND INFORMATION

Weight control has become a modern obsession. It is virtually a national pastime in the United States, where many tens of millions of Americans struggle daily with diets and exercise programs. Some are motivated by a desire to live a healthier lifestyle. Others are driven by a need to alleviate anxiety about personal appearance.

Digital scales are an important tool used by many in a program of weight control or management. Most digital scales known in the art do little more than measure and display a user's current weight using a digital measurement technology instead of a conventional mechanical measurement technology, such as a strain gauge. Other prior art digital scales may display additional information, such as recent weight loss or gain, or a calorie counter. However, the digital scales known in the art are generally ineffective in providing the individual with a full range of information useful to a successful program of weight control or management.

Many persons managing their weight need to know more than their current weight. For example, a safe weight control program usually begins with baseline information about the average expected range of weight for a particular person's body type. Many people may think they are either overweight or underweight, when in fact their weight may be normal for their age, height, sex, and frame type. Therefore, it would be desirable for a digital scale to give a person information about the desired weight range for a person of his or her body type.

Additionally, in order to measure progress, a person must keep a record of how his or her weight is changing over time. The reason for this is partly motivational. A record serves as a measure of progress and provides a person with feedback about their weight control program. However, an individual will typically write dates and weight measurements on a piece of paper that can be misplaced or discarded. Even if the handwritten record survives, the person is left with raw weight data and nothing more. Accordingly, it would be desirable for a digital scale to keep a record of a person's weight changes and convert that data into something more empirically useful, such as a historical graph of weight change over time or a record of the percent change in weight over a certain period.

An effective weight control program also usually includes control over the number of calories consumed. For example, people need specific guidance as to the number of calories that should be consumed to achieve, for example, weight loss of one pound a week. Once a person has attained a desired weight, he or she will want to know the number of calories to consume in order to maintain that weight. The appropriate number of calories, however, often changes over time, and few people are diligent enough to keep proper account of how calorie consumption should change given changes in weight. Charts and reference books offer some guidance, but any sort of research requires time that many people find hard to set aside. Accordingly, it would be desirable to provide a digital scale that displays such information for a user.

Although several prior art digital scales have attempted to provide one or more of these types of information to the user, there exists a need in the art for a scale that provides the user with several of these types of user-specific weight management information.

SUMMARY OF THE INVENTION

An exemplary embodiment of the present invention overcomes the above-described problems by providing a programmable microprocessor-controlled digital scale capable of storing profiles of multiple users and respective user-specific weight management information. A software program executed by the microprocessor creates and stores a user profile for each user. The user profile contains, for example, information about each user's age, sex, height, and body frame type. The software program also generates user-specific weight control information based on the user's profile and weight, and displays the information to the user. The generated user-specific weight control information can include, for example: current weight; absolute as well as percentage change in weight; graph of the minimum and maximum weight for the average person matching the user's profile; a thirty day rolling graph of the user's weight history; information about the number of calories that should be consumed in order to either maintain weight, or lose one pound per week; and body fat measurements.

DETAILED DESCRIPTION OF THE INVENTION

Various aspects of the system and method of the present invention will be described, and for purposes of explanation, specific configurations and details are set forth in order to provide a thorough understanding of the present invention. However, it will be apparent to one skilled in the art that the present invention may be practiced without these specific details. Furthermore, well known features have been omitted or simplified in order to prevent obscuring the present invention.

Figure 1:
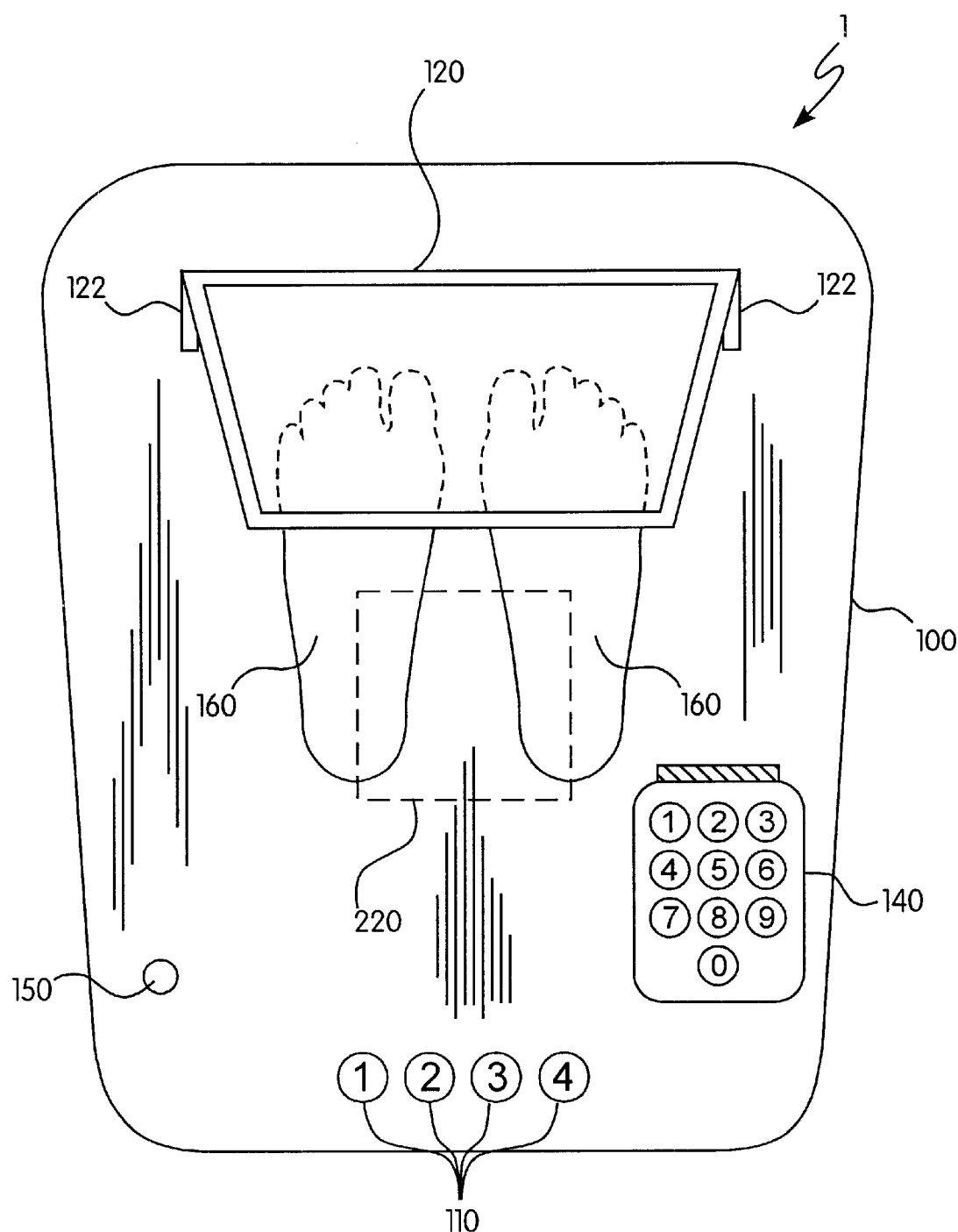
FIG. 1 illustrates a top view of a digital scale according to an exemplary embodiment of the present invention.

FIG. 1 illustrates the top surface of digital scale 1, and the various components mounted on its housing 100, according to an exemplary embodiment of the present invention. Housing 100 may be constructed of metal or a reinforced plastic, such as glass or carbon-filled polymers. Further, housing 100 may be manufactured in accordance with conventional manufacturing methods such as metal stamping or injection molding.

Figure 2:
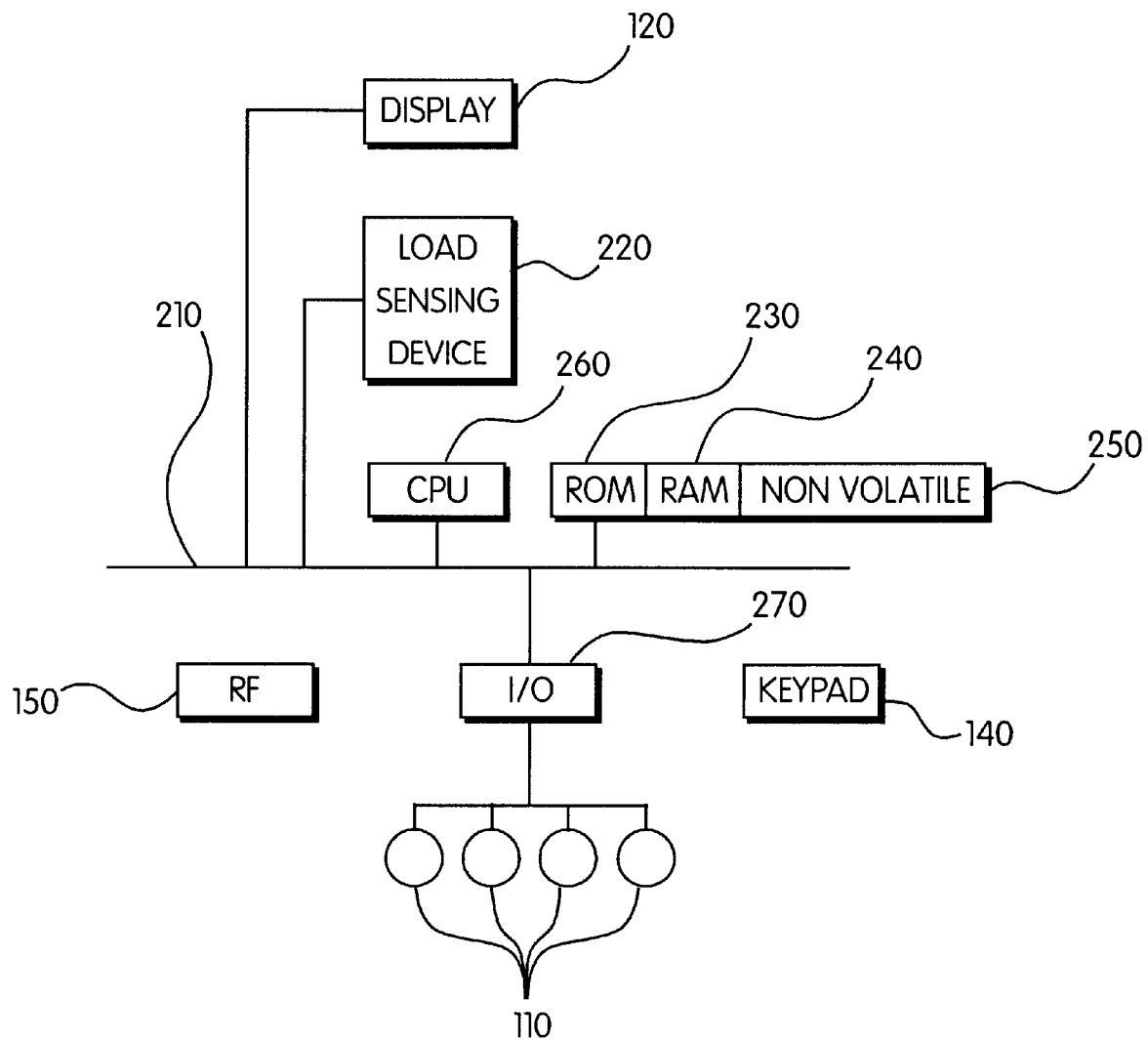
FIG. 2 is a block diagram illustrating the components of digital scale according to an exemplary embodiment of the resent invention.

Suitably mounted within housing 100 is a conventional load-sensing device 220, further depicted in FIG. 2. In this exemplary embodiment of the present invention, load sensing device 220 includes standard loadcell technology employed to measure weight and generate digital weight data capable of being read by, for example, a central processing unit (CPU) 260. Alternative means such as a conventional mechanical strain gauge and transducer coupled to an analog to digital converter may also be employed to perform weight measurements of a user.

The upper surface of housing 100 substantially above load-sensing device 220 includes, for example, two contoured and tactile foot-shaped surfaces 160. These contoured and tactile surfaces 160 cradle a user's foot and facilitate positive arch positioning as well as placement on the scale for accurate weight measurement. An alternative exemplary embodiment of the present invention may use a flat non-skid surface or other suitable surface instead of contoured and tactile surfaces 160.

Referring to FIG. 1, four depressible user profile selection buttons 110 are located on the upper surface of housing 100. Buttons 100 may be depressed, for example, by a user's toe. Alternative embodiments of the present invention may easily employ more or fewer user profile selection buttons 110 located in different locations on housing 100. Each profile selection button 110 is uniquely labeled (e.g., A, B, C, D or 1, 2, 3, 4) to identify different users. In this exemplary embodiment of the present invention, a different number is used to uniquely identify each button 110. In alternative embodiments, letters, names, or colors may be employed.

A digital display 120, employing standard LCD or LED technology, is suitably mounted on a plane parallel to, and slightly elevated above, the plane of the top surface of housing 100. In an exemplary embodiment of the present invention, the front part of a user's foot is partially covered by digital display 120 when the scale is used. Mounting digital display 120 in this way avoids the space limitations imposed on the top surface of housing 100. The digital display can be, for example, 3" high and 5" wide although other desired sizes may be utilized. In addition the display 120 may pivot somewhat about supports 122 to angularly adjust display 120, for example, via a hinged connection. This also allows for a digital display with a larger viewing area that can be angularly adjusted for easier reading by each user. Alternative embodiments may mount a smaller display 120 directly onto the top surface of housing 100.

User profile data entry buttons 140 provide a means for inputting user profile data and other pertinent weight control information into memory provided in the controller illustrated in FIG. 2. In this exemplary embodiment of the present invention, data entry buttons 140 take the form of a standard alpha-numeric keypad, similar to the touch-tone keypad utilized on conventional mobile telephones. Accordingly, in a conventional manner, a user can enter numerical digits and text characters as needed. The data entry buttons 140 may be hidden from view by a hinged or sliding panel located on and formed with the top surface of housing 100. An alternative means for inputting user profile data is provided by a standard RF sensing port 150 which may be used in conjunction with a keypad on a standard hand-held radio frequency (RF) transmitting device.

Again, referring to FIG. 1, operation of the digital scale 1 according to an embodiment of the present invention will be described. The user begins by selecting a user profile selection key 110 by depressing one of the keys 110. If the user has not already entered a user profile, the software program executed by the controller will prompt the user to do so.

The program prompts the user to input, for example, a name, age, height, sex and frame type, although not necessarily in that order. If the user has previously entered a user profile into memory, the program will retrieve that information from memory and display it for the user on digital display 120.

Next the user steps on digital scale 1 placing each foot in respective surface 160. In a conventional manner, the load sensing device 220 disposed within the housing 100 under surfaces 160 will determine the weight of the user (e.g., in pounds or kilograms) and pass the weight value for display on display 120 to the user. In an exemplary embodiment, digital display 120 will show the user a series of screens, one after the other, each with different user specific weight control information. According to an exemplary embodiment of the present invention, the first screen displays a summary of the user's profile such as the user's identity and age, height, frame type, etc. The next screen could then display the user's current weight. Next, the percent change in the user's weight since his last measurement can be displayed. Then, the amount of weight the user gained or lost since his last measurement. This is followed by a graph of the minimum and maximum weight of an average person matching the user's profile (e.g., determined through statistical data of the general population). A thirty day rolling graph appears next, showing how the user's weight has changed over time. Next, an overlay of the thirty day rolling graph is superimposed on top of the average user profile graph. Finally, a screen informs the user the number of calories he should consume to either maintain his weight or lose a certain amount of weight (e.g., one pound per week).

It should be apparent to those skilled in the art that additional information can be displayed as desired and in any desired order other than that described above. In an exemplary embodiment, the longer the user stands on digital scale 1, the more user specific weight control information that will be displayed. For example, digital scale 1 will continue to cycle through each screen and sequentially display them to the user until the user dismounts from digital scale 1. In alternate embodiments other methods of displaying weight control information may be used.

Figure 3:
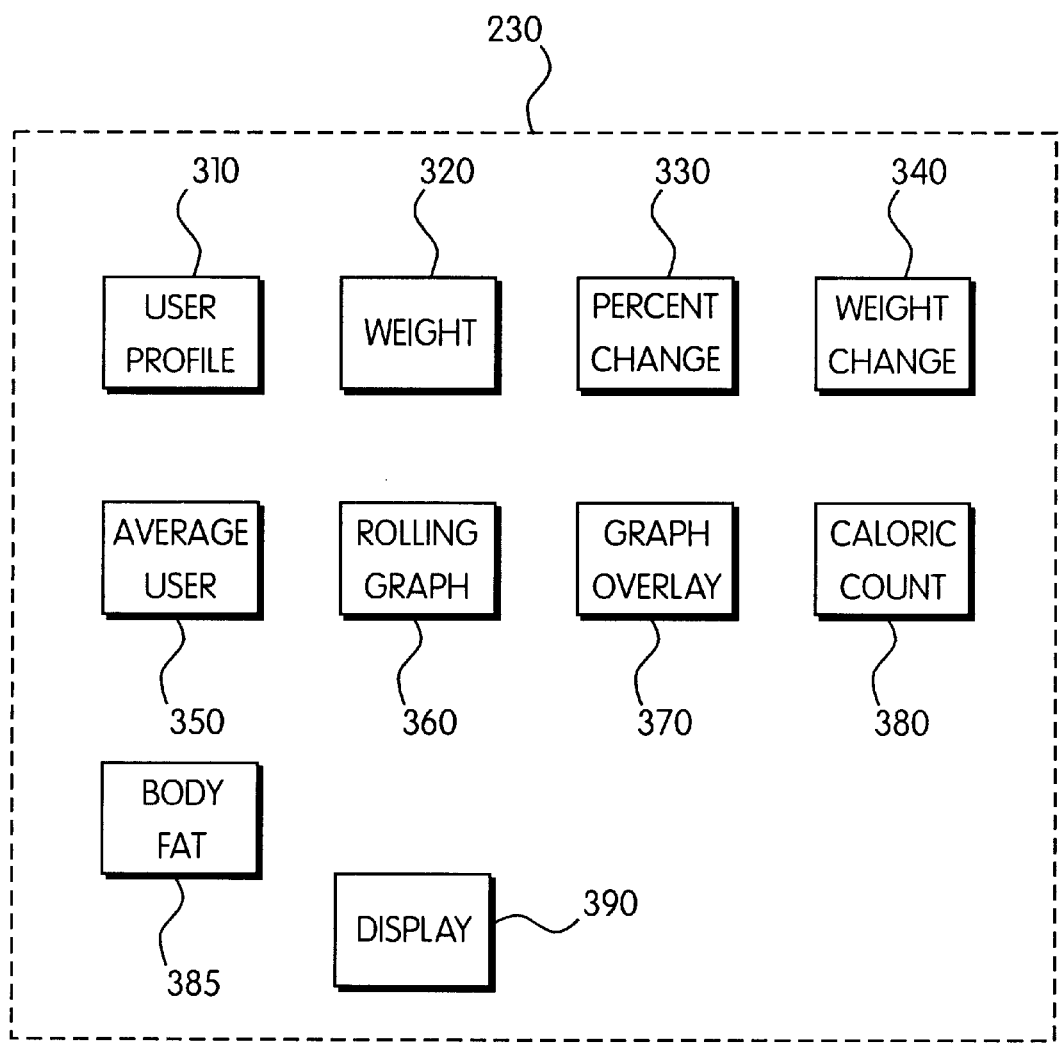
FIG. 3 is a block diagram illustrating software modules for generating weight control information according to an exemplary embodiment of the present invention.

FIG. 2 illustrates the major electronic components used in an exemplary embodiment of the present invention. The components depicted in FIG. 2 exchange data via, for example, a common data bus 210. The interconnecting lines shown in FIG. 2 are meant to show the movement of data, and do not limit the manner in which the various components can be electrically coupled. The electronic components contained inside housing 100 provide means for communicating user-specific input to the software modules, for example as illustrated in FIG. 3, in order for the software program to generate and display user-specific weight control information on display 120.

Referring to FIGS. 1 and 2, user profile data can be inputted using data entry buttons 140 or via RF sensing port 150. For example, the indication of previously entered user profile data is inputted for use by the appropriate software modules using selection keys 110 (e.g., depression of one of the keys 110). As shown in FIG. 1, up to four users can track weight management information in the scale 1.

Referring to FIG. 2, each of the input devices 110, 140 is electrically coupled to a standard input/output component (I/O) 270, such as an analog to digital (A/D) converter. I/O 270 is coupled, for example, to CPU 260 directly or via the common data bus 210. Thus, a user inputs information by actuating an input device which sends appropriate signals to I/O device 270. I/O device 270 translates these signals into digital data which are sent either directly to CPU 260 or via common data bus 210. CPU 260 executes the instructions of the software modules 310–390 stored in ROM 230. User-specific input is thereby made available for use by software modules 310–390 described in FIG. 3. As is known in the art, software modules 310–390 stored in 230 may be written in a conventional programming language such as C++ or assembly language and are executed by CPU 260 to generate user-specific weight control information. CPU 260 includes, for example, a conventional microprocessor or a microcontroller. The user-specific weight control information is output to digital display 120, which is coupled to CPU 260 via the common data bus 210.

Through the display module 390, the weight control data to the user for a predetermined amount of time such as ten seconds. In addition, display module 390 can display multiple sets of weight management information simultaneously (e.g., using a split screen presentation) or may sequentially and automatically display the weight management data generated by the respective software modules. Alternatively, the user can prompt the display of specific weight management data in a sequence and duration determined by the user, for example using a handheld RF controller or the keypad 140 to communicate with CPU 260 to select the desired information for display. In an exemplary embodiment, the user can be presented with a series of menu choices on the display and may select a desired menu choice (e.g., using the handheld RF device or the keypad 140), thus causing the selected weight management information to be displayed. If the user dismounts from digital scale 1 before a predetermined time expires, execution of the entire software program may terminate. If time expires for display of weight management data and the user remains standing on digital scale 1, execution of the software program may continue and the weight management data for the next software module may be displayed.

Referring to FIG. 3, the weight management program according to an embodiment of the present invention begins execution using, for example, the user profile module 310. Module 310 is responsible for storing and retrieving a user's profile. For example, a user actuates a user profile selection button 110 and module 310 checks a database file stored in non-volatile memory 250 to see if a user profile corresponding to the selected button already exists. If one does exists, the information is retrieved from the database and displayed on digital display 120. If a user profile does not already exist, the user profile module 310 prompts the user to enter, for example, a name, sex, age, height and frame type. Keypad 140 may be used in a conventional manner to enter the desired or requested information. User profile module 310 then stores the new user profile in, for example, a non-volatile memory area 250 and displays the user's profile on digital display 120. Execution of the weight management program is then passed to, for example, weight module 320. In an exemplary embodiment, the present invention may use a conventional relational database to store user information as well as weight management information, such as DB2 by International Business Machines of New York or MICROSOFT ACCESS by Microsoft Corporation of Washington.

Weight module 320 receives the current weight value for the user from load-sensing device 220 which is coupled to CPU 260 via common data bus 210. Weight module 320 then stores the current weight in, for example, a database in non-volatile memory 250, which may be the same or a different database storing the user information. Weight module 320 is also responsible for outputting the current weight value to digital display 120 via display module 390. Execution of the program is then passed to, for example, percent change module 330.

Percent change module 330 computes, for example, the percentage change in a user's weight since the last measurement. For example, this module accesses a database file stored in non-volatile memory 250, which may be the same or separate from the databases described above, to retrieve the user's last measured weight and calls weight module 360 to obtain the user's current weight. The percentage change information is sent to digital display 120 via the display module 390. Execution of the program is then passed to, for example, weight change module 340.

Weight change module 340 computes the difference between the user's last measured weight and a current weight value. This module retrieves, for example, information about the user's last measured weight from a database stored in non-volatile memory 250, which may the same as or separate from the databases described above, and calls weight module 320 to obtain the user's current weight. Module 340 causes the weight difference to be displayed on digital display 120, and execution of the program is then passed to average user profile module 350.

Average user profile module 350 generates, for example, a graph of the minimum and maximum weight measurements for the average person matching the user's profile. Module 350 interacts with, for example, user profile module 310 and compares the user's particular weight information to a database stored in, for example, ROM containing minimum and maximum weight values for an average person most closely matching the user's profile. For example, weight data for multiple body types, height, age and sex are readily available and can be stored in ROM 230 so that most users of the scale will fall within one of the pre-selected categories of stored weight data. Module 350 then causes the display of the average profile weight information as a graph on digital display 120. Execution of the program is passed to, for example, rolling graph module 360.

Rolling graph module 360 generates, for example, a rolling graph of the history of the user's weight changes during the last 30 days. This module obtains a user's weight history, for example, from a database stored in non-volatile memory, which again can be the same or separate from previously described databases. The rolling graph is displayed on digital display 120 and execution of the program is passed to, for example, graph overlay module 370.

Graph overlay module 370 superimposes the 30 day graph generated by rolling graph module 360 onto the average user profile graph generated by average user profile module 350. The graph overlay module then displays the combined graphs on digital display 120. Execution of the program is finally passed to, for example, calorie count module 380.

Calorie count module 380 computes, for example, the number of calories the user should consume in order to either maintain his or her weight or to lose a certain weight (e.g., one pound per week). This module interacts with weight module 320 to obtain information about the user's current weight, and also interacts with the user profile module 310 to obtain information about the user's profile. Then calorie count module 380 compares this information with a calorie consumption table stored, for example, in ROM 230 and generates a calorie count value for the user. This value is then displayed to the user on the digital display via display module 390. Execution of the program is passed back to user profile module 310. The program loops until the user terminates the program by dismounting from digital scale 1.

Body fat module 385 computes, for example, body fat or fat tissue of the user or other human body composition values such as lean tissue or body water. One known method for measuring a user's body fat utilizes "bio-impedance."

For example, two electrical contacts can be integrally formed in tactile surfaces 160 so that each foot of a user is in contact with an electrical contact. A low voltage signal passed between the contacts and thus through the user's body allows the user's body impedance to be measured. A suitable known body fat algorithm included in body fat module 38 can be executed by CPU 260 and operate on the user's impedance value to generate a body fat measurement in a manner known in the art. The resultant body fat value can be displayed to the user via display module 390. Alternatively, two electrical contacts can be provided in a handheld RF controller such that placement of the thumb and forefinger of each hand of user an electrical contact when an electrical signal is passed between the contact and thus through the user results in an impedance value of the user that can be measured and correlated to a body fat value in a manner known in the art. The algorithm to process the impedance value can be stored in the handheld RF device and the calculated value passed back to the CPU 260 or the impedance value can be transmitted to the CPU 260 from the RF controller so that body fat module 385 can calculate the body fat value. The body fat value, or any other value or item of weight management information calculated by the system and method of the present invention, may be displayed using a graph or other method.

Figure 4:
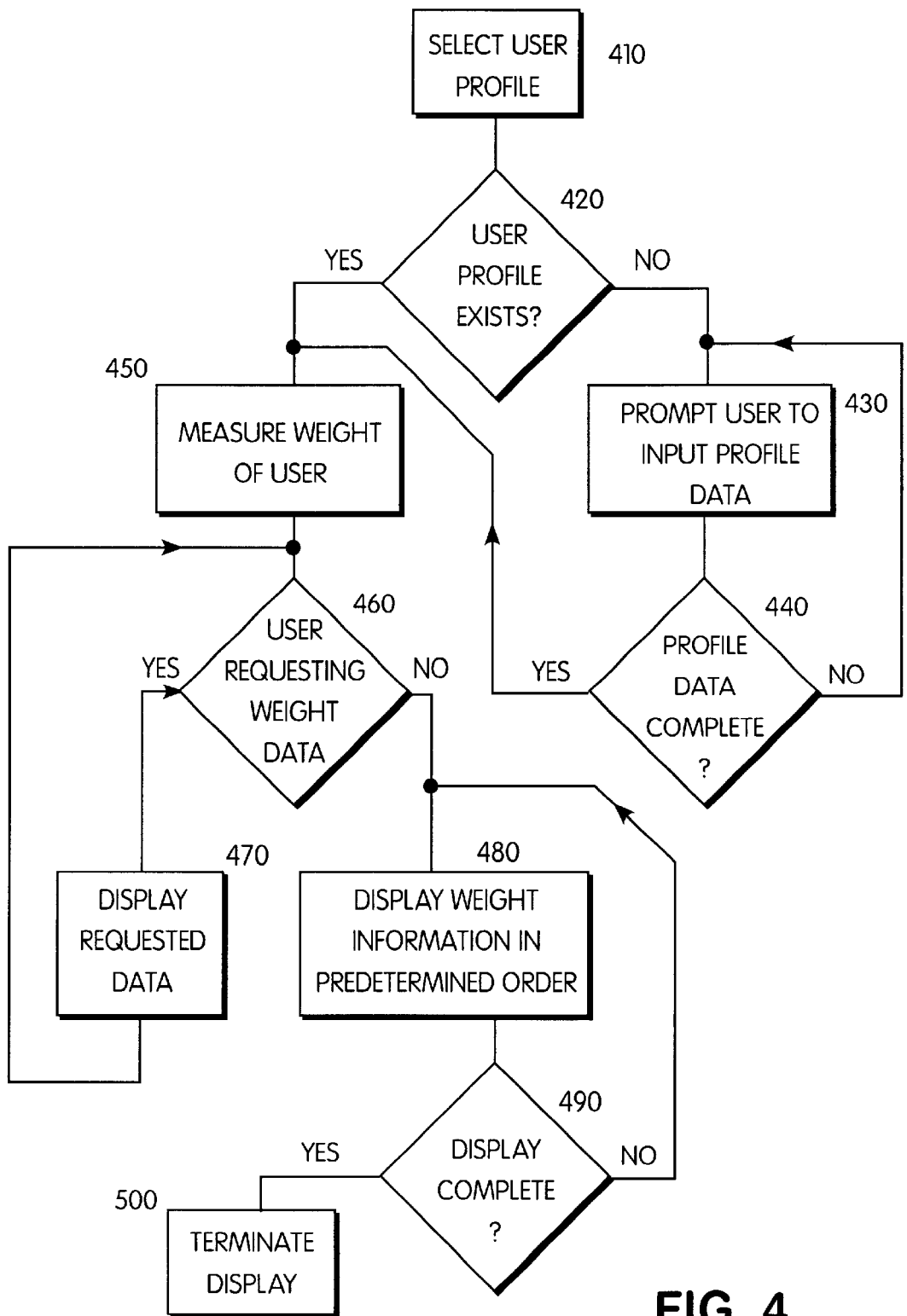
FIG. 4 illustrates an exemplary flowchart for the operation of a weight management scale according to an embodiment of the present invention.

FIG. 4 illustrates an exemplary flowchart for the operation of a weight management scale according to an embodiment of the present invention. At 410, a user selects a user profile, for example by depressing a tactile button 110. At 420 it is determined if a user profile exists for the selected button. If no profile exists, then the user will be prompted at 430 to enter user profile information, such as name, age, height, body type and sex. The scale receives the user information. Other data may be requested as is deemed appropriate. The process loops back to 430 until all user data has been input. Alternately, the user may input only certain of the user data.

Once the user has supplied all of the needed information as determined at 440, the weight of the user is determined at 450, for example using the loadcell or strain gauge measurement sensor located in the housing of the scale.

At 460, the user may request specific weight management information be displayed, for example in response to a prompt to the user of available weight management information. If the user requests specific data, it is displayed at 470 and the process loops back to 460.

If no specific information is requested by the user, then at 480 weight management information is automatically displayed to the user in, for example, a predetermined order, the process looping back to 480 until all available information has been displayed. Once all of the user-specific weight management information has been displayed at 490, the program terminates at 500.

Alternately, if a user makes no specific request, no automatic weight management information display need be performed, or weight management information may be displayed in another manner. For example, random weight management data may be displayed. In alternate embodiments other sequences of steps may be used to implement the system and method of the present invention. Other types and combinations of user data or weight measurement information may be input and output.

While the system and method of the present invention is described with respect to specific embodiments, it should be noted that the invention may be implemented in different manners. Since numerous modifications and variations will readily occur to those skilled in the art, it is not desired to limit the invention to the exact construction and operation shown and described, and accordingly, all suitable modifications and equivalents may be resorted to, falling within the scope of the present invention.

What is claimed is:

1. A digital weight measurement device, comprising:
   a housing;
   a weight sensor disposed in the housing;
   a graphic display capable of displaying multiple sets of weight management information, the graphic display being mounted on an upper surface of the housing; and
   a controller disposed in the housing and coupled to the weight sensor and the display,
   wherein the controller comprises a microprocessor coupled to a memory and the microprocessor generates a user profile, a graph display, a number of calories to be consumed in order to achieve a predetermined weight, and a body fat value, and
   wherein the controller causes at least one of a plurality of user-specific weight management information to be transmitted to the display.

2. The digital weight measurement device of claim 1, wherein the plurality of user-specific weight management information includes at least one of a current weight of the user, a percentage change in weight, a graph of a minimum and a maximum weight for an average person matching a profile of the user, a thirty day rolling graph of the user's weight history, a number of calories to be consumed in order to achieve a predetermined weight, and a predetermined body fat measurement.

3. The digital weight measurement device of claim 1, wherein the weight sensor includes loadcell technology.

4. The digital weight measurement device of claim 1, wherein the memory includes a read only memory portion storing computer readable means for causing the microprocessor to perform at least one of:
   generating the user profile,
   generating a percent change value,
   generating a weight change value,
   generating an average user display,
   generating a rolling graph display,
   generating a graph overlay display,
   generating a calorie count display,
   generating the body fat value, and
   displaying at least one of the user profile, the percentage change value, the weight change value, the average user display, the rolling graph display, the graph overlay display, the calorie count display and the body fat value.

5. The digital weight measurement device of claim 1, comprising a keypad disposed in the housing and coupled to the controller, the keypad providing for a user input of data.

6. The digital weight measurement device of claim 5, wherein the keypad provides for entry of alphanumeric data.

7. The digital weight measurement device of claim 1, comprising a radio frequency input port disposed on the housing and coupled to the controller, the radio frequency input port cooperating with a radio frequency handset, the radio frequency handset providing for a user input of data.

8. The digital weight measurement device of claim 1, comprising a contoured surface disposed on an upper surface of the housing substantially above the weight sensor, the contoured surface receiving feet of a user.

9. The digital weight measurement device of claim 1, wherein the display is movably mounted on a support extending from the upper surface of the housing.

10. The digital weight measurement device of claim wherein the display includes one of a LCD display and a LED display.

11. The digital weight measurement device of claim 5, wherein the data includes at least one of a user sex, a user age, a user height, and a user frame, and the controller performs at least one of:

generating the user profile, generating a percent change value, generating the body fat value, and displaying at least one of the user profile, the percentage change value, and the body fat value.

12. The digital weight measurement device of claim 5, wherein the keypad includes a set of user keys, each user key corresponding to a different user.

13. A method of displaying, via a scale, weight management information to a user comprising:

receiving a user profile selection, wherein if the selected user profile does not exist, prompting the user to enter user profile information and creating the user profile based on input from the user;

determining the weight of the user and the body fat value of the user;

determining a number of calories to be consumed in order to achieve a predetermined weight;

generating at least one of a display of a minimum and a maximum weight of an average person matching a profile of the user, a rolling graph display, and a graph overlay display; and displaying weight management information for the user.

14. The method of claim 13 wherein the user profile includes an age, a height, and a sex.

15. The method of claim 14 wherein the user profile includes a user identifier, and wherein multiple user profiles may be entered.

16. The method of claim 13 comprising:

if no specific weight management information request is received, displaying a predetermined weight management information value.

17. The method of claim 16 comprising:

displaying weight management information in a predetermined order.

18. The method of claim 14 comprising:

if no specific weight management information request is received, displaying a predetermined weight management information value.

19. The method of claim 14 comprising:

displaying weight management information in a predetermined order.

20. The method of claim 14 wherein the weight management information includes the percent change in the user's weight.

21. The method of claim 15, wherein the weight management information includes a graph.

22. The method of claim 13 comprising:

if a specific weight management information request is received, displaying said specific weight management information.

23. A digital weight measurement device, comprising:

a housing;

a weight sensor disposed in the housing;

a graphic display capable of displaying multiple sets of weight management information, the graphic display being mounted on an upper surface of the housing; and a controller disposed in the housing and coupled to the weight sensor and the display, wherein the controller comprises a microprocessor coupled to a memory and the microprocessor generates a number of calories to be consumed in order to achieve a predetermined weight and at least one of a current weight of the user, a percentage change in weight, a graph of a minimum and a maximum weight for an average person matching a profile of the user, a rolling graph of the user's weight history, a graph overlay display, and a body fat value, and wherein the controller causes at least one of these values to be displayed by the display in a predetermined order or in an order determined by the user.

* * * * *